United States Patent [19]

Clune et al.

[11] 4,011,601
[45] Mar. 15, 1977

[54] PROSTHETIC HEART VALVE

[75] Inventors: Michael Francis Clune, Oneonta; John Richard Shanebrook, Schenectady, both of N.Y.

[73] Assignee: Research Corporation, New York, N.Y.

[22] Filed: Oct. 14, 1975

[21] Appl. No.: 622,061

[52] U.S. Cl. .................................. 3/1.5; 137/527.8
[51] Int. Cl.² .......................................... A61F 1/22
[58] Field of Search .......... 3/1.5; 137/527.4, 527.8, 137/527

[56] References Cited
UNITED STATES PATENTS

| | | | |
|---|---|---|---|
| 2,934,084 | 4/1960 | Adams | 137/527.4 |
| 3,367,364 | 2/1968 | Cruz et al. | 3/1.5 X |
| 3,370,305 | 2/1968 | Goot et al. | 3/1.5 |
| 3,534,411 | 10/1970 | Shiley | 3/1.5 |
| 3,538,514 | 11/1970 | Schimert et al. | 3/1.5 |
| 3,546,711 | 12/1970 | Bokros | 3/1.5 |
| 3,926,215 | 12/1975 | Macleod | 3/1.5 X |

*Primary Examiner*—Ronald L. Frinks
*Attorney, Agent, or Firm*—Harold L. Stowell

[57] ABSTRACT

A prosthetic heart valve wherein the occluder member is of high camber air-foil-like configuration which assists in creating vortices in the blood flow pattern into the ventricular cavity. The formed vortices aid in cleansing the cavity and in closing the valve during contraction of the cavity.

7 Claims, 7 Drawing Figures

PROSTHETIC HEART VALVE

BACKGROUND OF THE INVENTION

The leaflets of the human mitral and tricuspid valves help establish an orderly pattern of blood flow into the left and right ventricles. For example, the anterior leaflet of the mitral valve extends diagonally across its ventricular cavity, separating it into inflow and outflow tracts. The resulting flow pattern in the left ventricle consists of vortices that aid in cleansing the ventricular cavity and in closing the valve such that little, if any, regurgitation occurs upon contraction of the ventricle.

SUMMARY OF THE INVENTION

The present invention is directed to an improved heart valve construction which produces flow characteristics that are similar to those of the natural mitral and tricuspid valves between the left atrium and left ventricle and between the right atrium and right ventricle, respectively. Hereinafter, these valves will be simply referred to as the ventricular valve.

The invention may be defined as a prosthetic ventricular heart valve comprising an occluder disc having upstream and downstream curvilinear faces. The downstream face is concave and the upstream face is convex. The concave and convex faces define a high camber airfoil-like structure having a leading edge and a trailing edge with the thickness of airfoil-like structure being greater in the region of the leading edge than in the region of the trailing edge. Means are provided for supporting the occluder disc for limited rotational and longitudinal movement about an axis between the leading and trailing edges of the disc. Further, the support means provides a seat for the marginal portion of the upstream curvilinear face of the disc, all as to be more fully described hereinafter.

BRIEF DESCRIPTION OF THE DRAWING

The invention will be more particularly described with reference to the drawing wherein.

DESCRIPTION OF PREFERRED EMBODIMENT

Figure 1:
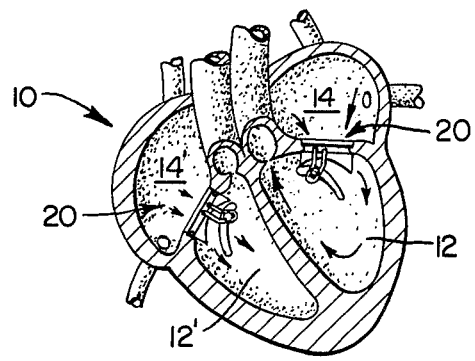
FIG. 1 is a somewhat diagrammatic section through a human heart illustrating the positioning of the valve, of the invention, as a replacement for the mitral and the tricuspid valves of the heart.
Figure 2:
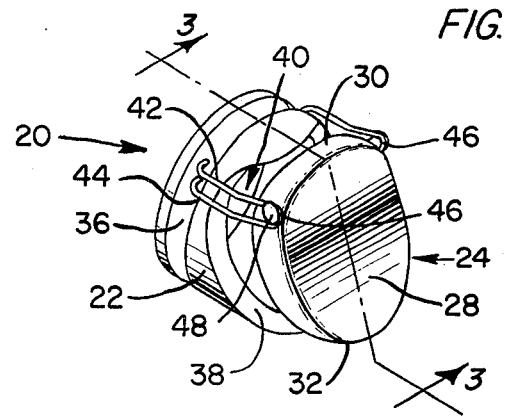
FIG. 2 is a perspective view of the valve unit of the invention.

Referring to FIG. 1 of the drawing, 10 generally designates a human heart having left and right ventricles 12 and 12' respectively and left and right atriums 14 and 14' respectively. In the human heart, these chambers are separated by leaflet type tricuspid and mitral valves which in FIG. 1 are shown replaced by the improved prosthetic heart valve generally designated 20.

As more clearly shown in FIGS. 2–6, the improved prosthetic heart valve includes a base member 22 and an occluder disc generally designated 24.

The occluder disc 24 has an upstream curvilinear face 26 and a downstream curvilinear face 28. The upstream face is convex and the downstream face 28 is concave.

The pair of faces 26 and 28 generally define a high camber airfoil-like structure having a leading edge portion 30 and a trailing edge portion 32. It will be noted from FIG. 2 that the thickness of the airfoil-like disc is greater in the region of the leading edge portion 30 than in the region of the trailing edge portion 32.

The disc 24 is made of biocompatible resilient material. Particularly good results are obtainable with silicone type rubbers such as Silastic of Dow Corning, a composition of organosiloxane polymers.

The base member 22 is generally cylindrical in transverse cross-section and is provided at the upstream end with a groove 36 adapted to receive a conventional attaching or sewing collar forming no part of the present invention.

The downstream end 38 of the base member 22 forms a seat for the marginal portion of the upstream face of the occluder disc 24.

The base member may be constructed of any nonresilient biocompatible material and useful results may be obtained by constructing the base member from Stellite of the Haynes Stellite Company, a non-ferrous alloy containing cobalt, chromium, tungsten, carbon and silicon. Another suitable material for construction of the base member is pyrocarbon.

The base member 22 is provided with means for mounting the occluder disc 24 for limited rotational and longitudinal movement relative to the base member 22. The illustrated mounting means comprises a pair of track-forming members generally designated 40. Each of the pair of track-forming members 40 includes a pair of spaced rails 42 and 44 closed at their downstream end 46. The opposite ends of the rails 42 and 44 are secured in the groove 36, which receives the sewing collar.

Figure 3:
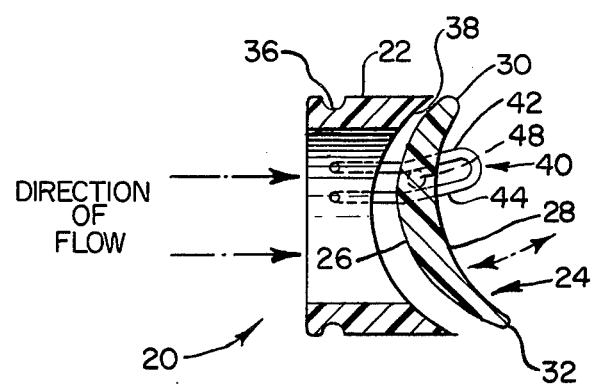
FIG. 3 is a sectional view of the valve shown in FIG. 2 with the valve disc in a partially open position.
Figure 4:
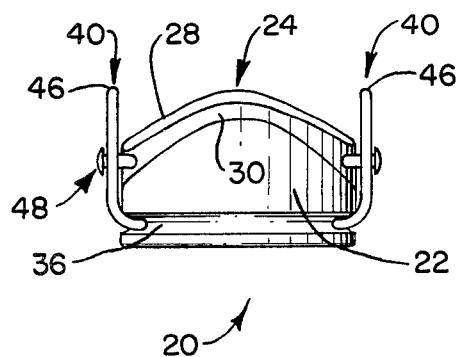
FIG. 4 is an elevational view of the valve unit looking toward the leading edge portion of the valve disc.
Figure 5:
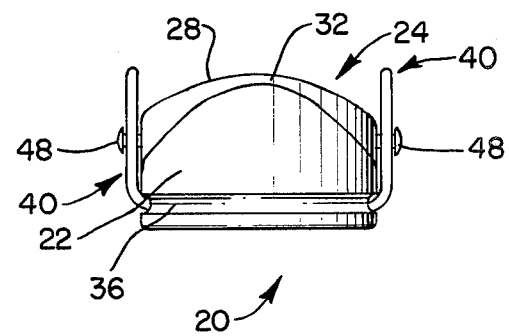
FIG. 5 is an elevational view of the valve unit looking toward the trailing edge portion of the valve disc.
Figure 6:
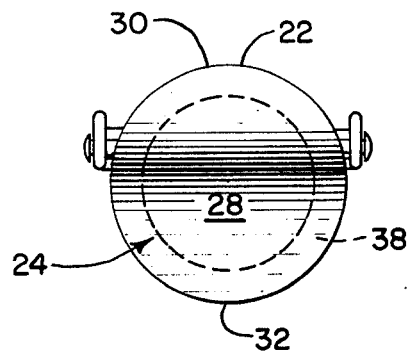
FIG. 6 is a top plan view of the valve unit.

Cooperating with the track-forming members 40 are a pair of pivot pins 48 which extend from the peripheral surface of the occluder disc 24, closer to the leading edge 30 than the trailing edge 32 as more clearly shown in FIGS. 3 and 6 of the drawings. The pivot pins 48 are received between the rails 42 and 44 so that there is limited rotational and longitudinal movement about an axis between the leading and trailing edges of the disc 24. As the valve opens the first movement of the disc 24, relative to the base member 22, is longitudinally downstream. After the disc has initially moved downstream so that its upstream face 26 has moved out of contact with its seating engagement with surface or end 38 of the base member 22, the disc is free to rotate about the axis of the pivot pins 48.

Figure 7:
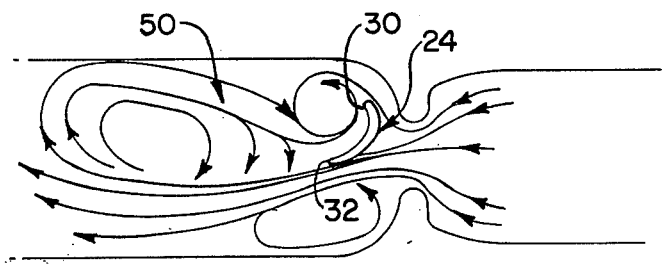
FIG. 7 is a sketch of streamlines of the valve of the present invention obtained from a test chamber.

Referring now to FIG. 7, which is a sketch of streamlines of a valve of the present invention obtained from a test chamber, with flow in the direction of the streamlines, it will be noted that the main flow is about the trailing edge 32 of the disc 24 with a minor flow about the leading edge 30. Further, from an inspection of the streamlines, it will be noted that vortices are generated as with a natural heart valve with the main vortices, indicated at 50, having a tendency to act on the downstream face of the occluder disc 24 which aid in closing the valve when the ventricle chamber commences to contract. This closing assistance together with low pressure losses results in substantial improvements in artificial ventricular construction.

The vortices which are generated by the airfoil-like occluder disc also determine the amount of opening of the improved heart valve. It has been observed that the generated vortices acting against the downstream face 28 of an occluder disc 24, constructed as shown in the drawings, control the rotational movement of the disc and provide a very natural blood flow pattern into the ventricles of the human heart.

While a specific shape of the high camber airfoil-like disc is shown in the drawing, good results would be obtained through the use of other subsonic high camber airfoil-like configurations.

We claim:

1. A prosthetic heart valve comprising a base member and an occluder disc having upstream and downstream curvilinear faces, the downstream face being concave, and the upstream face being convex, said concave and convex faces defining a high camber airfoil-like structure having leading and trailing edge portions, means supporting the occluder disc for (a) movement longitudinally downstream relative to the base member to move the upstream face out of seating engagement with said base member, and (b) rotational movement about an axis between the leading and trailing edges of the disc and means on said base member providing a seat for the marginal portion of the upstream curvilinear face of the disc said seat providing means having a curved profile that matches the curved profile of the upstream curvilinear face of the occluder disc.

2. The invention defined in claim 1 wherein the supporting means for the occluder disc comprise a pair of spaced track-forming members secured at one end to the external wall of the base member and extending generally in a downstream direction and a pair of pivot pins secured to the periphery of the occluder disc between the leading and trailing edges thereof received between each pair of track forming members.

3. The invention defined in claim 2 wherein the pivot pins are closer to the leading edge of the disc than the trailing edge thereof.

4. The invention defined in claim 1 wherein the occluder disc comprises silicone rubber and the base member comprises a non-resilient biocompatible material.

5. The invention defined in claim 4 wherein the base member comprises a non-ferrous cobalt-chromium alloy.

6. The invention defined in claim 4 wherein the base member comprises pyrocarbon.

7. A prosthetic heart valve comprising an occluder disc having upstream and downstream curvilinear faces, the downstream face being concave, and the upstream face being convex, said concave and convex faces defining a high camber airfoil-like structure having leading and trailing edge portions, the thickness of the airfoil-like disc being greater in the region of the leading edge portion than in the region of the trailing edge portion, means supporting the occluder disc for (a) movement longitudinally downstream relative to the base member to move the upstream face out of seating engagement with said base member, and (b) rotational movement about an axis between the leading and trailing edges of the disc and means on said base member providing a seat for the marginal portion of the upstream curvilinear face of the disc said seat providing means having a curved profile that matches the curved profile of the upstream curvilinear face of the occluder disc.

* * * * *